(12) United States Patent
Choi et al.

(10) Patent No.: US 8,009,292 B2
(45) Date of Patent: Aug. 30, 2011

(54) SINGLE POLARIZER FOCUSED-BEAM ELLIPSOMETER

(75) Inventors: Yong Jai Choi, Daejeon (KR); Won Chegal, Daejeon (KR); Hyun Mo Cho, Daejeon (KR)

(73) Assignee: Korea Research Institute of Standards and Science (KR)

( * ) Notice: Subject to any disclaimer, the term of this patent is extended or adjusted under 35 U.S.C. 154(b) by 0 days.

(21) Appl. No.: 12/666,159

(22) PCT Filed: Nov. 11, 2008

(86) PCT No.: PCT/KR2008/006640
§ 371 (c)(1),
(2), (4) Date: Dec. 22, 2009

(87) PCT Pub. No.: WO2009/064102
PCT Pub. Date: May 22, 2009

(65) Prior Publication Data
US 2010/0296092 A1    Nov. 25, 2010

(30) Foreign Application Priority Data
Nov. 13, 2007    (KR) .................. 10-2007-0115398

(51) Int. Cl.
*G01J 4/00*    (2006.01)
(52) U.S. Cl. ...................................... 356/369
(58) Field of Classification Search .................. None
See application file for complete search history.

(56) References Cited

U.S. PATENT DOCUMENTS

| | | | |
|---|---|---|---|
| 3,985,447 A | 10/1976 | Aspnes | |
| 5,042,951 A | 8/1991 | Gold et al. | |
| 5,166,752 A | 11/1992 | Spanier et al. | |
| 5,608,526 A | 3/1997 | Piwonka-Corle et al. | |
| 6,031,614 A * | 2/2000 | Michaelis et al. | 356/369 |

(Continued)

FOREIGN PATENT DOCUMENTS
KR    10-0742982    6/2006

OTHER PUBLICATIONS

Masetti et al., In Situ Monitoring of film deposition with an ellipsometer based on a four detector photopolarimeter, Oct. 1996, Applied Optics, vol. 35, No. 28, pp. 5626-5629.*

(Continued)

*Primary Examiner* — Gregory J Toatley
*Assistant Examiner* — Juan D Valentin
(74) *Attorney, Agent, or Firm* — Cantor Colburn LLP

(57) ABSTRACT

The present invention relates to a single-polarizer focused-beam ellipsometer. An ellipsometer according to the present invention includes a light source (210); a beam splitting part (220) for splitting a light generated in the light source (210) into a polarized light; an objective lens (230) for concentrately irradiating some of light split by the beam splitting part (220) onto a specimen (240); a photodetector (250) for detecting the light passed through the objective lens 230 and the beam splitting part (220) after reflected from the specimen (240) with unit cells; and a central processing unit (260) for correcting the intensity of the light detected by the photodetector (250) into a value corresponding to the unit cell of the photodetector (250) along multiple incidence plane passage of 360° with respect to respective incidence angles and processing the corrected value.

12 Claims, 6 Drawing Sheets

U.S. PATENT DOCUMENTS

| | | |
|---|---|---|
| 6,753,961 B1 | 6/2004 | Norton et al. |
| 6,833,920 B2 | 12/2004 | Rassman et al. |
| 6,898,537 B1 | 5/2005 | McGahan |
| 2004/0042009 A1* | 3/2004 | Aspnes et al. ................. 356/369 |
| 2004/0233439 A1* | 11/2004 | Mieher et al. ................. 356/401 |
| 2008/0018895 A1* | 1/2008 | Opsal ........................... 356/365 |

OTHER PUBLICATIONS

International Search Report-PCT/KR2008/006640 dated Dec. 22, 2008.

* cited by examiner

SINGLE POLARIZER FOCUSED-BEAM ELLIPSOMETER

TECHNICAL FIELD

The present invention relates to a single-polarizer focused-beam ellipsometer, and more particularly, to a focused-beam ellipsometer having a simplified structure in which a single polarizing beam splitter plays roles a polarization generator, a beam splitter and a polarization analyzer. Herein, a novel measuring method is employed in which a method of measuring variation in polarization state of a light reflected by a specimen with respect to multiple planes of incidence is applied to multiple angles of incidence, and thus it is possible to analyze exact information for optical properties of the specimen, i.e., in the case of a thin film, thickness and refractive index of the thin film.

BACKGROUND ART

The present invention relates to an ellipsometer and is a technology of measuring variation in polarization state which a light incident to a surface of a specimen with a specific polarization state comes to have after being reflected and analyzing the measured value, thereby finding out optical physical properties of the specimen. Particularly, a variety of nano-thin film manufacturing processes is used in semiconductor industries, and an ellipsometer which is non-destructive and contactless real-time measuring equipment is widely used as a measuring equipment to evaluate physical properties of the manufactured thin films.

A variety of ellipsometers is used not only in the semiconductor industries but also in research institutions such as a university, and is classified, according to how the light used as a probe is incident to the specimen, into a type in that a parallel light is incident to a specimen in an inclined direction (U.S. Pat. No. 3,985,447), a type in that a light is focused onto a specimen in an inclined direction using an optical system (U.S. Pat. No. 5,166,752 and U.S. Pat. No. 5,608,526), and a type in that a light is focused onto a specimen in a vertical direction using an optical system (U.S. Pat. No. 5,042,951 and U.S. Pat. No. 6,898,537).

In the case that a parallel light is incident in an inclined direction, the ellipsometer has excellent measuring accuracy since it is possible to accurately control an angle of incidence as all light rays are irradiated onto the specimen with the same incidence angle, but it is difficult to reduce a size of a beam incident to the specimen to less than a mm since diffraction is increased when reducing the size of the incident beam using an iris.

In semiconductor industries, a wafer particularly provided with a measuring region limited in an area of tens μm×tens μm is used to evaluate the variety of thin film manufacturing processes for the manufacture of semiconductor devices through the measurement. In order to measure the thickness of the thin film within the measuring region limited in the micrometer level using an ellipsometer, a technology of focusing a parallel light incident in an inclined direction on the surface of a specimen using an optical system consisting of a lens or a reflective mirror is used. However, in this case, it is difficult to ensure and maintain the measuring accuracy compared to using the parallel in an inclined direction since light rays having a plurality of incidence angles are incident to the specimen at the same time.

As a critical dimension patterned in a wafer is expected to be continuously reduced with recent continuous development in a semiconductor device manufacturing technology, the area of the limited measuring region have to be correspondingly reduced. However, in the case of the inclined directional focused-beam ellipsometer, it is actually difficult to reduce the size any more due to barrier such as aberration and structural limitation of the focused-beam optical system despite of many studies and efforts for reducing the area of the light beam irradiated onto the specimen as small as possible.

The vertical-incident focused-beam ellipsometer permits the measurement within a fine pattern region having smaller area since it is able to focus a parallel light incident in a vertical direction onto the surface of the specimen in a size of several μm using an objective lens.

FIG. 1 shows a basic structure of the vertical-incident focused-beam ellipsometer (U.S. Pat. No. 5,042,951) which is currently widely used. The focused-beam ellipsometer is provided with a polarization generator 130 for making a parallel light 120 emitted from a light source 110 into a specific polarization state, a non-polarizing beam splitter 140 for splitting some of the light passed through the polarization generator 130, an objective lens 150 for refracting and concentrately irradiating the light split by the non-polarizing beam splitter 140 onto a specimen 160, a polarization detector 170 for filtering only the specific polarization state from the light passed through the objective lens 150 and the non-polarizing beam splitter 140 after reflected from the specimen 160, and a photodetector 180 having pixels for detecting an intensity of the light passed through the polarization detector 170.

Meanwhile, U.S. Pat. No. 6,898,537 suggests that by placing a single linear polarizer, instead of the polarization generator 130 and the polarization detector 170 of the conventional focused-beam ellipsometer, is installed in the non-polarizing beam splitter 140 and objective lens 150 and rotated by a motor, and a spectroscopic photodetector is employed as the photodetector, and it is therefore possible to analyze the light refracted by patterned specimen.

Such the conventional patent technology has a relatively complex structure and necessarily requires a calibration process for finding out an optical axes of the polarization generator 130 and the polarization detector 170 with respect to the reflection face of the non-polarizing beam splitter 140 for the accurate measurement, since the polarization generator 130, the non-polarizing beam splitter 140 and the polarization detector 170 are separately installed as shown in FIG. 1 or some optical component can be rotated.

DISCLOSURE OF THE INVENTION

It is an object of the present invention to provide a novel principle of a focused-beam ellipsometer, in which a construction of an apparatus is simplified by replacing functions of the polarization generator, the polarization detector and the beam splitter with a single polarizing beam splitter and a measuring precision is enhanced by employing a measuring method in which a measurement on multiple planes of incidence is applied to multiple angles of incidence.

An ellipsometer according to the present invention includes a light source (210); a beam splitting part (220) for splitting a light generated in the light source (210) into a polarized light; an objective lens (230) for concentrately irradiating some of light split by the beam splitting part (220) onto a specimen (240); a photodetector (250) for detecting the light passed through the objective lens 230 and the beam splitting part (220) after reflected from the specimen (240) with unit cells; and a central processing unit (260) for correcting the intensity of the light detected by the photodetector (250) into a value corresponding to the unit cell of the photodetector (250) along multiple incidence plane passage of 360° with respect to respective incidence angles and processing the corrected value.

The beam splitting part (220) is a polarizing beam splitter (221).

Alternately, the beam splitting part (220) may include a linear polarizer and a non-polarizing beam splitter.

The photodetector (250) includes a two-dimensional imaging device consisting of a plurality of unit cells.

The light source (210) includes a white light source selected from a tungsten-halogen lamp, a xenon discharge lamp or a monochromatic light source such as a laser.

The objective lens (230) includes an optical system having any one selected from the group consisting of a lens, a mirror and a combination of the lens and the mirror.

The ellipsometer may further include a collimating optical system (270) provided between the light source (210) and the beam splitting part (220) and making the light emitted from the light source 210 into a parallel light.

In the case that the light source (210) is a white light source, the ellipsometer may further include a plurality of band-pass filters (211) radially disposed at the back of the light source (210) or in front of the photodetector (250) and allowing a specific range of wavelength of the light emitted from the light source (210) to pass therethrough and a filter wheel (212) rotatable so that the light selectively passes through the band-pass filter (211).

The ellipsometer may further include an optical system (251) provided with a relay lens for improving measuring performance of the photodetector (250).

The ellipsometer may further include a two-dimensional imaging device for observing an image of the surface of the specimen.

The ellipsometer may further include a specimen support for supporting the specimen, the specimen support being provided with a transporter for making the specimen support to be movable in forward and rearward direction and left and right direction and rotatable.

The ellipsometer may further include a compensator (280) provided in front of the objective lens (230) and compensating the light split by the beam splitting part or an electrical polarization modulator provided in front of the objective lens (230) and capable of controlling phase difference of the light split by the beam splitting part with an electricity.

The compensator (280) includes a rotator for rotating the compensator (280) on the vertical axis of the specimen (240).

The single-polarizer focused-beam ellipsometer according to the present invention has a simple structure compared to a conventional focused-beam ellipsometer by employing a single polarizing beam splitter and is expected to have improved measuring accuracy as the measurement for a single plane of incidence is extended to the measurement for multiple planes of incidence and multiple angles of incidence. Therefore, use of the measuring apparatus according to the present invention allows more accurate measurement for the information for optical properties of the specimen, i.e., in the case of a thin film, thickness and refractive index of the thin film.

Also, the single-polarizer focused-beam ellipsometer according to the present invention can remove a signal noise due to motor vibration and an error due to rotation of optical components, as it allows the measurement for an ellipsometric constant without a constant driving part by a stepping motor or a DC motor, compared to conventional rotating analyzer type, rotating polarizer type and rotating compensator type ellipsometers which are currently widely used. Therefore, it has an advantage that measuring accuracy is relatively improved and measuring speed is improved as fast as the driving speed of the photodetector.

Also, the single-polarizer focused-beam ellipsometer according to the present invention has an advantage of measuring the optical properties of the specimen more accurately by taking polarization components for the multiple planes of incidence of 360° with respect to multiple angles of incidence from 0 degree to the maximum angle of incidence in a static state in which there is no motor driving for the optical components, compared to conventional focused-beam ellipsometer which takes the polarization properties on a single plane of incidence.

DETAILED DESCRIPTION OF MAIN ELEMENTS

Figure 1:
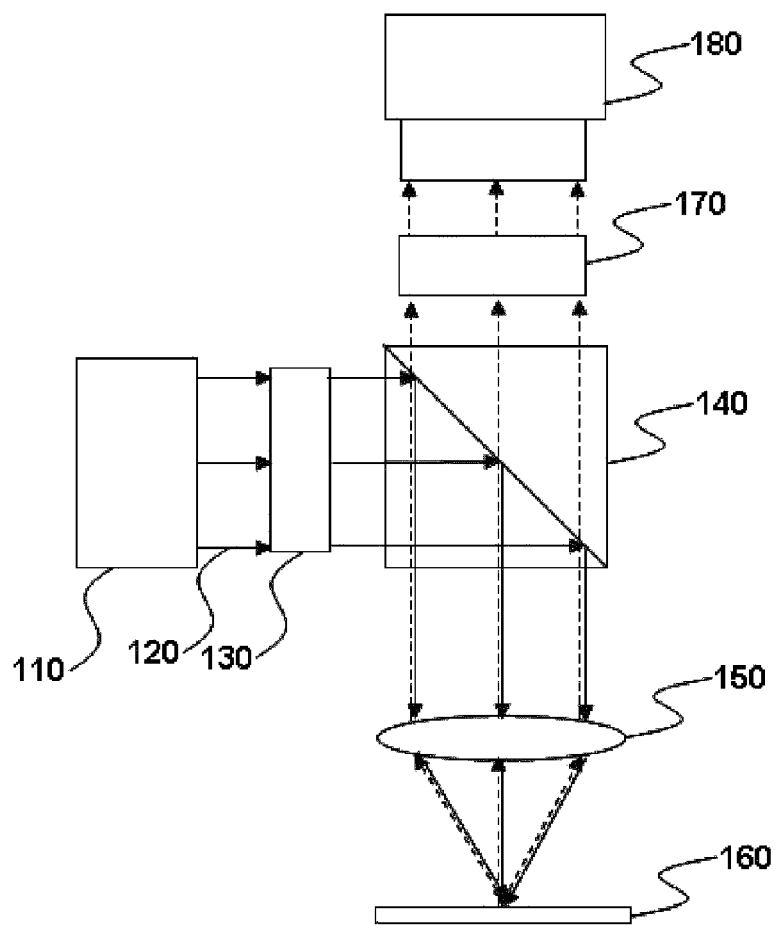
FIG. 1 is a view illustrating a representative structure of a focused-beam ellipsometer according to a conventional art.

110, 210: light source
120: parallel light
130: polarization generator
140: non-polarizing beam splitter
150, 230: objective lens
160, 240: specimen
170: polarization detector
180, 250: photodetector
211: band-pass filter
212: filter wheel
213: motor
220: beam splitting part
221: polarizing beam splitter
251: optical system
260: central processing unit
270: collimating optical system
280: compensator

BEST MODE FOR CARRYING OUT THE INVENTION

Herein after, preferred embodiments of an ellipsometer according to the present invention will be described in detail with reference to accompanying drawings.

Figure 2:
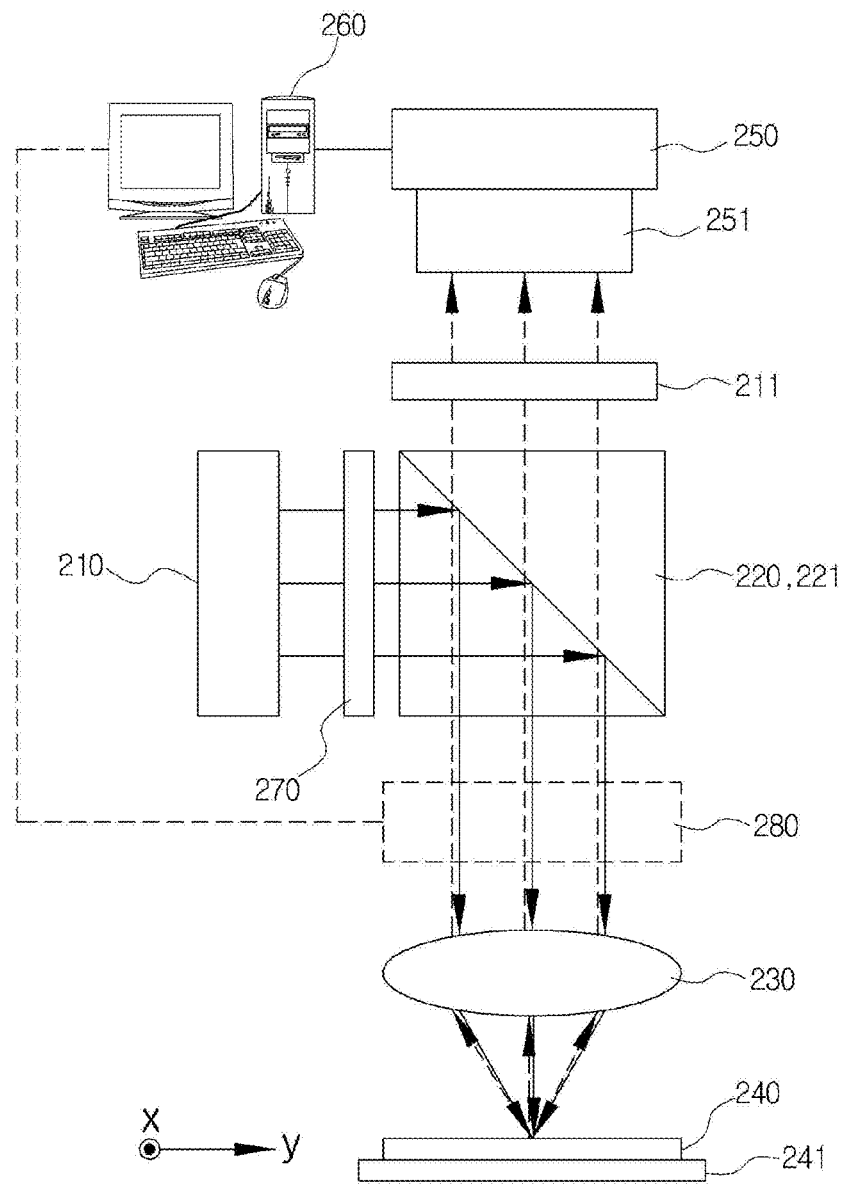
FIG. 2 is a view illustrating a structure of a single-polarizer focused-beam ellipsometer according to the present invention.
Figure 3:
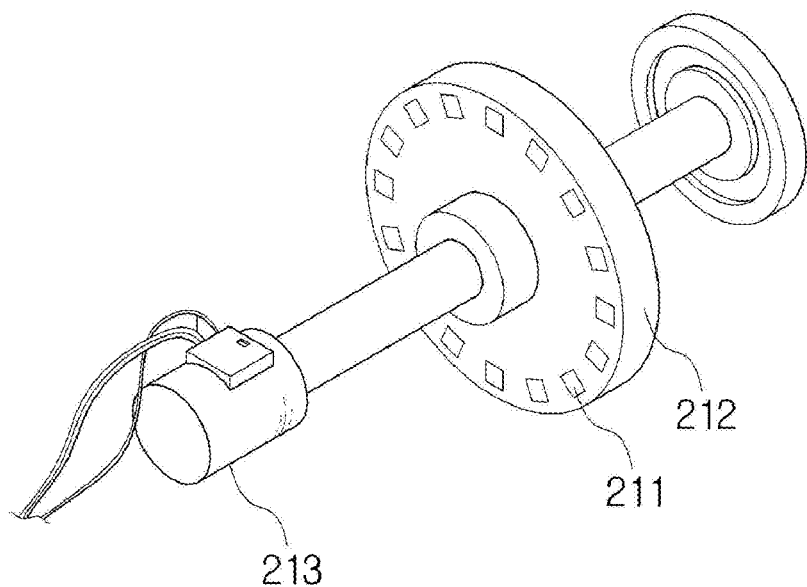
FIG. 3 is a perspective view illustrating a filter wheel according to the present invention.
Figure 4:
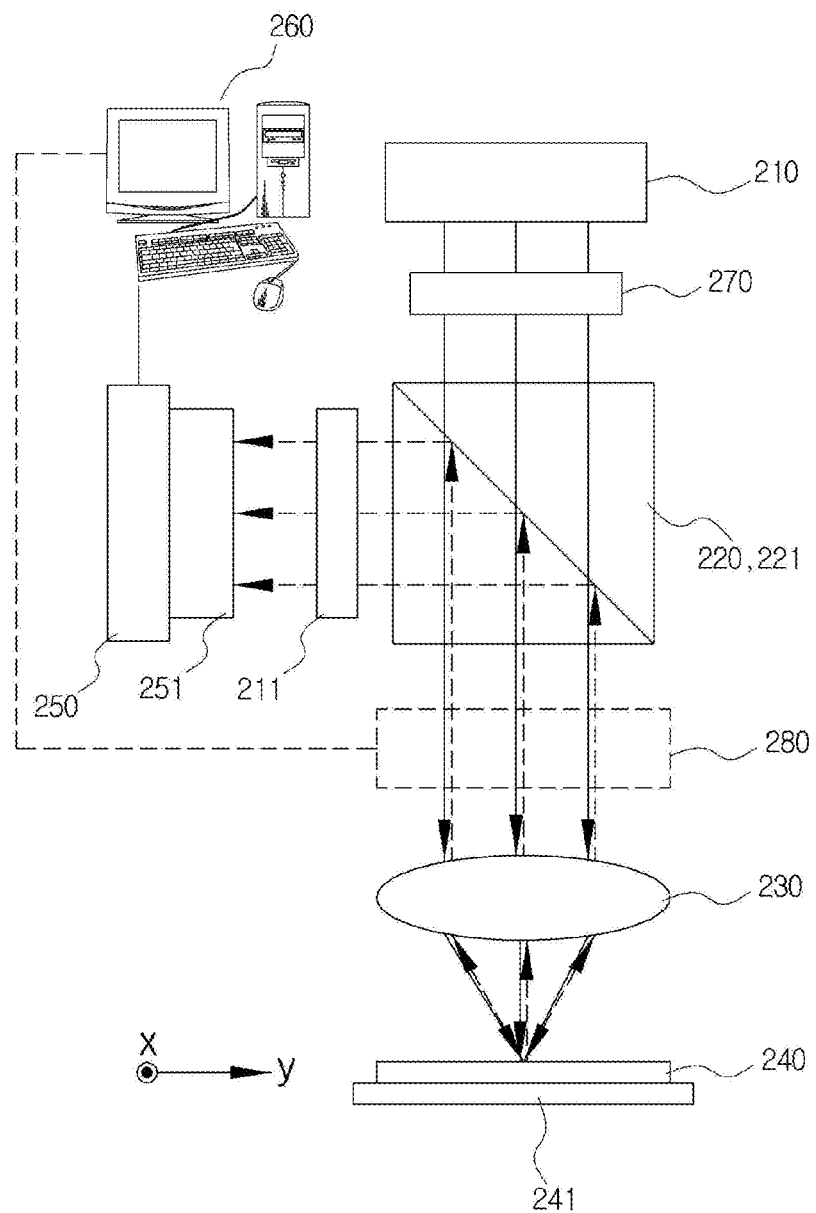
FIG. 4 is a view illustrating another embodiment of the single-polarizer focused-beam ellipsometer according to the present invention, in which locations of a light source and a photodetector are interchanged.
Figure 5:
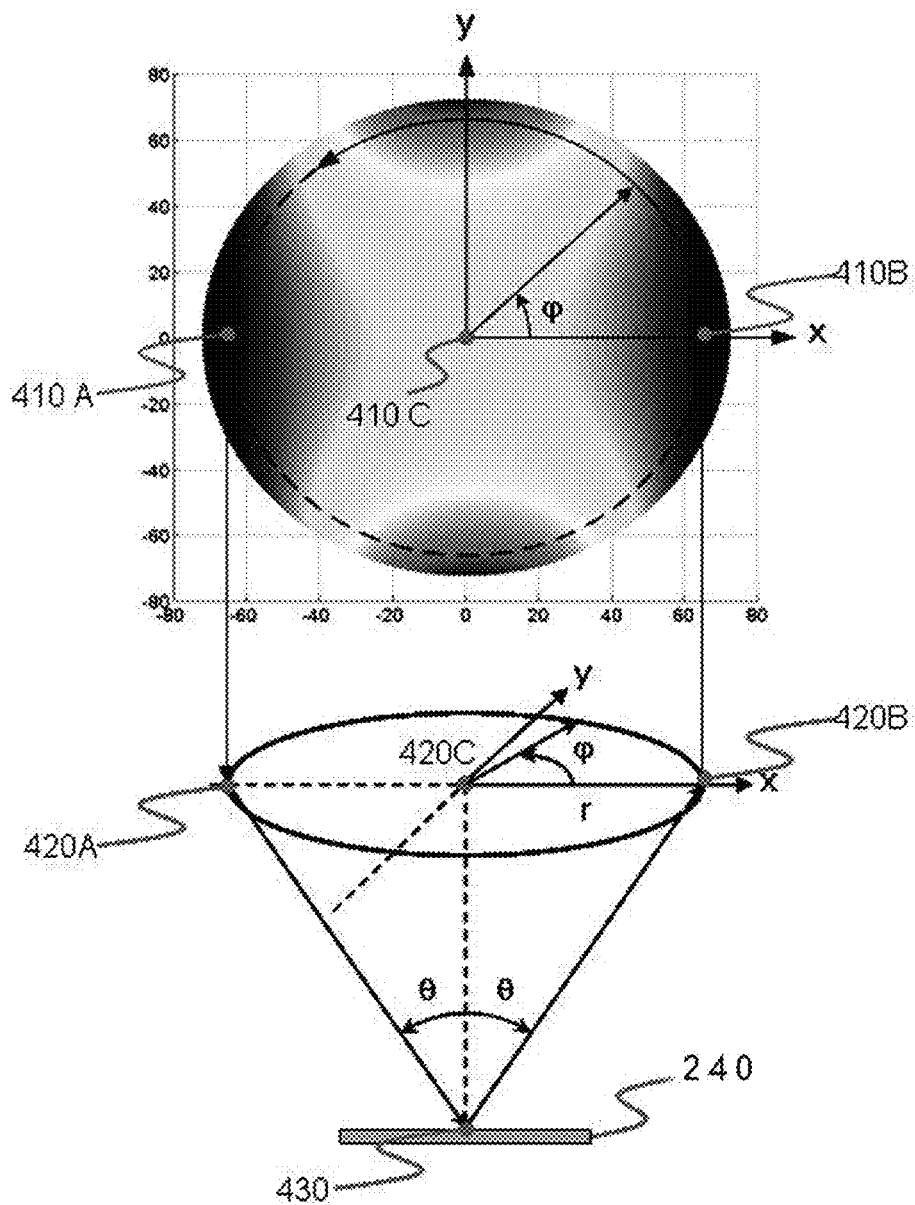
FIG. 5 is a two-dimensional image illustrating distribution of the light intensity signal measured by the photodetector.
Figure 6:
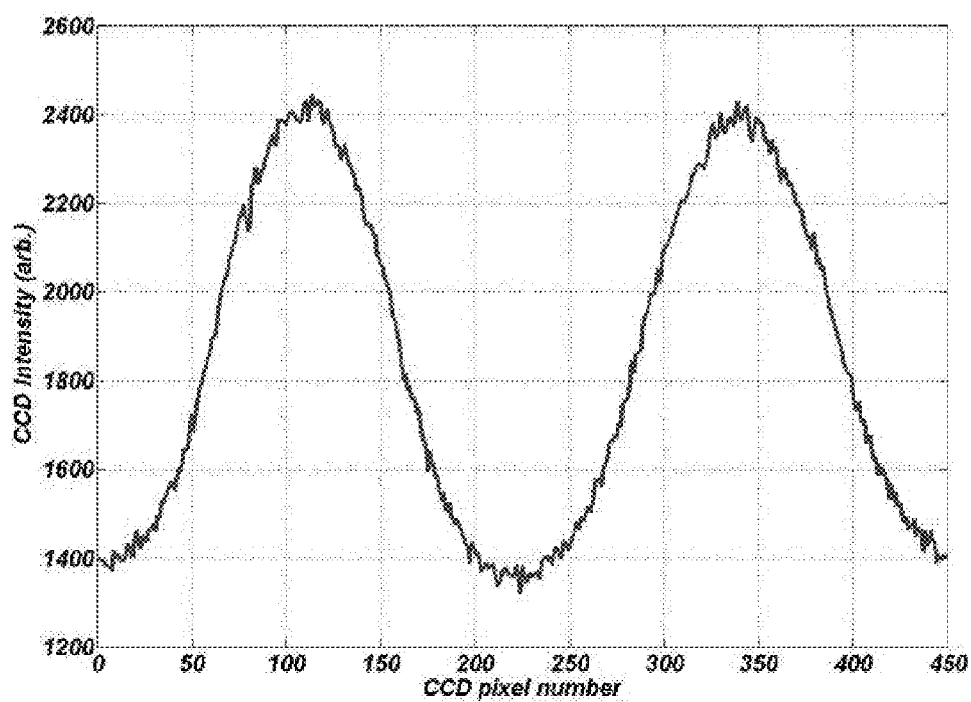
FIG. 6 is a graph illustrating the light intensity signal measured by pixels of the photodetector placed on a circumference with a fixed radius which rotates in a counterclockwise direction around the object lens, i.e. on a passage of multiple planes of incidence as shown in FIG. 4.

FIG. 2 is a view illustrating a structure of a single-polarizer focused-beam ellipsometer according to the present invention; FIG. 3 is a perspective view illustrating a filter wheel according to the present invention; FIG. 4 is a view illustrating another embodiment of the single-polarizer focused-beam ellipsometer according to the present invention, in which locations of a light source and a photodetector are interchanged; FIG. 5 is a two-dimensional image illustrating distribution of the light intensity signal measured by the photodetector; and FIG. 6 is a graph illustrating the light intensity signal measured by unit cells of the photodetector placed on a circumference with a fixed radius which rotates in a counterclockwise direction around the object lens, i.e. on a passage of multiple planes of incidence as shown in FIG. 4.

As shown, an ellipsometer according to the present invention for measuring optical physical properties of specimen such as thickness and refractive index of a thin film includes a light source 210; a beam splitting part 220 for splitting a light generated in the light source 210 into a polarized light; an objective lens 230 for concentrately irradiating some of the light split by the beam splitting part 220 onto a specimen 240; a photodetector 250 for detecting the light passed through the objective lens 230 and the beam splitting part 220 after reflected from the specimen 240 with unit cells; and a central processing unit 260 for correcting the intensity of the light detected by the photodetector 250 into the value corresponding to the unit cell of the photodetector 250 along multiple incidence plane passage of 360° with respect to respective incidence angles and processing the corrected value.

The light source 210 may include a white light source such as a tungsten-halogen lamp, a xenon discharge lamp and a monochromatic light source such as a laser which are generally used in the art.

In the case that a white light source is used as the light source 210, it is preferable that a band-pass filter 211 for allowing a specific range of wavelength of the light emitted from the light source 210 to pass therethrough is placed at the back of the light source 210 or in front of the photodetector 250. At this time, as shown in FIG. 3, the band-pass filter is radially arranged, and preferably, further includes a filter wheel 212 rotatable so that the light selectively passes through the band-pass filter 211. The filter wheel 213 is rotated by a motor 213. Preferably, the motor 213 is a stepping motor. FIG. 2 illustrates that the band-pass filter 211 is placed in front of the photodetector 250.

The beam splitting part 220 acts to split the light generated in the light source 210 into a polarized light. Preferably, the beam splitting part 220 is a polarizing beam splitter 221. Also, in the present invention, the polarizing beam splitter 221 vertically reflects some of the light and transmits the rest of the light, and the respective lights have specific polarization states.

The light emitted from the light source 210 is made to a parallel light using a reflection and refraction optical system, and some of the light is reflected by the polarizing beam splitter 221 in FIG. 2, of which polarization direction has a characteristic of being aligned in an X-axis direction parallel to the inclined reflection face within the polarizing beam splitter 221.

The split light is vertically focused on the surface of the specimen 240 by the objective lens 230 with a large numerical aperture (NA) placed below the polarizing beam splitter 221. At this time, a specimen support 241 for supporting the specimen 240 is further provided and the specimen support 241 is preferably transported by a transporter movable in forward and rearward direction and left and right direction and rotatable.

In addition, an optical system having any one selected from the group consisting of a lens, a mirror and a combination of the lens and the mirror is preferably used as the objective lens 230.

Furthermore, a compensator 280 may be further provided between the polarizing beam splitter 221 and the objective lens 230 so as to control the polarization state of the light incident to the specimen 240.

The compensator 280 is for compensating, in front of the objective lens 230, the light split by the beam splitting part 220. The compensator 280 arbitrarily controls the polarization state of the light incident to the specimen 240, and changes, between the polarizing beam splitter 221 and the objective lens 230, the phase of the progressive wave according to the polarization state.

The compensator 280 has a characteristic that when the linearly polarized light is vertically incident to the surface of the compensator 280, it has the value of phase difference between the light transmitted when the polarization direction is parallel to the light axis of the compensator 280 and the light transmitted when the polarization direction is vertical to the light axis of the compensator 280.

In addition, an electrical polarization modulator capable of controlling phase difference of the light split by the beam splitting part with electricity may be provided in front of the objective lens 230 instead of the compensator 280.

Also, the compensator 280 is preferably further provided with a rotator for rotating the compensator 280 on the vertical axis of the specimen 240.

Also, the beam splitting part 220 may include a linear polarizer and a non-polarizing beam splitter instead of the polarizing beam splitter 221. At this time, the linear polarizer is placed between the non-polarizing beam splitter and the compensator 280.

Further, the ellipsometer preferably further includes a collimating optical system 270 for making the light emitted from the light source 210 into a parallel light.

The photodetector 250 detects the light reflected from the specimen 240 and passed through the objective lens 230 and the beam splitting part 220 with its unit cells. Herein, the photodetector 250 is preferably provided with a two-dimensional imaging device which has a plurality of unit cells and is able to observe an image of the surface of the specimen by measuring two-dimensional light intensity image. At this time, an example of the imaging device includes a charge-coupled device (CCD).

Also, an optical system 251 provided with a relay lens is preferably provided to improve the measuring performance of the photodetector 250.

Information obtained from the respective unit cells of the photodetector 250 is transferred to the central processing unit 260 and stored as a digital signal.

The central processing unit 260 acts to correct the intensity of the light detected by the photodetector 250 into a value corresponding to the unit cell of the photodetector 250 along multiple incidence plane passage of 360° with respect to respective incidence angles and processing the corrected value. A voltage or current signal detected by the photodetector 250 analyzed with respect to its waveform through a computer, i.e. the central processing unit 260, thereby extracting optical properties of the specimen, e.g. in the case of a thin film, thickness and optical constants of the thin film.

The same function will be performed even when the locations of the light source and the photodetector 250 are interchanged as shown in FIG. 4 unlike FIG. 2.

Hereinafter, the principle of the vertical-incidence beam-focused ellipsometer of the present invention will be described in detail.

A chart in an upper part of FIG. 5 is a two-dimensional image illustrating distribution of the light intensity signal measured by the photodetector 250. An angle θ of incidence of the light incident onto the center 420C of the objective lens 230 is 0, and all the lights incident onto the circumference with the same radius r have the same angle θ of incidence and the plane of incidence is rotated according to a value of azimuth φ.

In the case that a parallel light in a specific polarization state is incident onto 420A, the light is refracted toward the point 430 on the surface of the specimen 240 by the objective lens 230 with the angle θ of incidence, then reflected with the angle θ of reflection, then arrived at the position 420B symmetrical with respect to the center 420C of the objective lens 230, and then refracted by the objective lens 230 to become a parallel light again. After that, only the polarization component parallel to a Y-axis direction is filtered while the light is transmitted through the polarizing beam splitter 221, and then arrived at the position 410B having an azimuth φ of 0 on X-axis in the two-dimensional image signal obtained by the photodetector 250. At the position 410B, the intensity of the corresponding light is finally detected as an electric signal such as voltage or current by the pixel of the photodetector 250.

Likewise, in the case of being incident onto 420B, the light passes through 420A after being reflected from the surface of the specimen 240, and then is detected at the position 410A of the photodetector 250. The light incident to every position of the objective lens 230 passes through the position symmetrical with respect to the center 240 of the objective lens 420C. At this time, the light incident to a position on the circumference with a radius of r of the objective lens has the same angle θ of incidence.

The parallel light incident onto the objective lens 230 is incident onto the surface of the specimen 240 with being refracted by NA of the objective lens 230, and herein, the maximum angle $\theta_{max}$ of incidence of the light incident onto surface of the specimen 240 is determined as follows by NA of the objective lens 230:

$$\theta_{max}=\sin^{-1}(NA)$$

FIG. 6 illustrates a graph in which an electric signal for the intensity of the light detected by the photodetector 250 is corrected into a value in the center of the photodetector 250 corresponding to the respective unit cells of the photodetector 250 [for example, if the photodetector is a CCD, the unit cell is a pixel] along a passage of multiple planes of incidence generated on a circumference with fixed radius of r and then processed. Though simple calculation, the intensity signal of the light detected by the photodetector 250 is generally expressed by the following equation:

$$I(\phi)=I_0[1+\alpha_2\sin(2\phi)+\alpha_4\sin(4\phi)+\beta_2\cos(2\phi)+\beta_4\cos(4\phi)]$$

where, $I_0$ is a mean value of the intensity of the light detected on the circumference with fixed radius of r, and $\alpha_2$, $\alpha_4$, $\beta_2$ and $\beta_4$ are Fourier constants.

Therefore, the values of $\alpha_2$, $\alpha_4$, $\beta_2$ and $\beta_4$ are obtained by Fourier transforming data on one circle of the various concentric circles to the center axis 420C of the objective lens 230 in the two-dimensional image data measured for the light intensity. In general, two of these Fourier constants have non-zero value.

The optical properties of the specimen is found out by obtaining Fourier constants determined by the multiple incidence plane measurement with respect to the respective angles of incidence from the center axis 420C to the maximum angle $\theta_{max}$ of incidence of the objective lens, i.e. with respect to multiple angles of incidence and analyzing the constants. Since the measurement method with respect to the multiple planes of incidence can obtain a similar effect to conventional rotating analyzer type ellipsometer or rotating polarizer type ellipsometer, the multiple incidence plane measuring method with respect to the multiple angles of incidence is expected to raise the measuring accuracy compared to the conventional focused-beam ellipsometer using a single plane of incidence.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An ellipsometer comprising:
   a light source (210);
   a beam splitting part (220) for splitting a light generated in the light source (210) into a polarized light;
   an objective lens (230) for concentrately irradiating some of light split by the beam splitting part (220) onto a specimen (240);
   a photodetector (250) for detecting the light passed through the objective lens 230 and the beam splitting part (220) after reflected from the specimen (240) with a plurality of unit cells; and
   a central processing unit (260) which acquires values measured in the plurality of unit cells corresponding to different azimuthal angles for a same circumference at a predetermined radius to take polarization components for multiple incident surfaces of 360° in a static state to acquire a measurement value based on a change in polarization direction of light incident on the surface of the specimen.

2. The ellipsometer as set forth in claim 1, wherein the beam splitting part (220) is a polarizing beam splitter (221).

3. The ellipsometer as set forth in claim 1, wherein the beam splitting part (220) includes a linear polarizer and a non-polarizing beam splitter.

4. The ellipsometer as set forth in claim 1, wherein the photodetector (250) includes a two-dimensional imaging device consisting of a plurality of unit cells.

5. The ellipsometer as set forth in claim 1, wherein the light source (210) includes a white light source selected from a tungsten-halogen lamp, a xenon discharge lamp or a monochromatic light source such as a laser.

6. The ellipsometer as set forth in claim 1, further comprising a collimating optical system (270) provided between the light source (210) and the beam splitting part (220) and making the light emitted from the light source 210 into a parallel light.

7. The ellipsometer as set forth in claim 5, wherein in the case that the light source (210) is a white light source, the ellipsometer is further comprises a plurality of band-pass filters (211) radially disposed at the back of the light source (210) or in front of the photodetector (250) and allowing a specific range of wavelength of the light emitted from the light source (210) to pass therethrough and a filter wheel (212) rotatable so that the light selectively passes through the band-pass filter (211).

8. The ellipsometer as set forth in claim 6, further comprising an optical system (251) provided with a relay lens for improving measuring performance of the photodetector (250).

9. The ellipsometer as set forth in claim 7, further comprising a two-dimensional imaging device for observing an image of the surface of the specimen.

10. The ellipsometer as set forth in claim 7, further comprising a specimen support for supporting the specimen, the specimen support being provided with a transporter for making the specimen support to be movable in forward and rearward direction and left and right direction and rotatable.

11. The ellipsometer as set forth in claim 1, further comprising a compensator (280) provided in front of the objective lens (230) and compensating the light split by the beam splitting part or an electrical polarization modulator provided in front of the objective lens (230) and capable of controlling phase difference of the light split by the beam splitting part with an electricity.

12. The ellipsometer as set forth in claim 11, wherein the compensator (280) includes a rotator for rotating the compensator (280) on the vertical axis of the specimen (240).

* * * * *